United States Patent [19]

Wu et al.

[11] 4,297,518
[45] Oct. 27, 1981

[54] DECOMPOSITION OF CUMENE HYDROPEROXIDE WITH A HOMOGENEOUS CATALYST

[75] Inventors: Ching-Yong Wu, O'Hara Township, Allegheny County; Wayne R. Pretzer, Oakmont; Thaddeus P. Kobylinski, Gibsonia, all of Pa.

[73] Assignee: Gulf Research & Development Company, Pittsburgh, Pa.

[21] Appl. No.: 852,923

[22] Filed: Nov. 18, 1977

[51] Int. Cl.³ .................. C07C 27/00; C07C 45/00; C07C 49/08; C07C 39/04

[52] U.S. Cl. .................................... 568/385; 568/798

[58] Field of Search ................. 260/593 A; 568/798, 568/385

[56] References Cited

U.S. PATENT DOCUMENTS 2,663,735  12/1953  Filar et al. ..................... 260/593 A

FOREIGN PATENT DOCUMENTS 51-80830  7/1976  Japan.

Primary Examiner—Joseph E. Evans
Attorney, Agent, or Firm—Deane E. Keith; Forrest D. Stine; Donald L. Rose

[57] ABSTRACT

Cumene hydroperoxide in a solvent comprising phenol and acetone is decomposed to phenol and acetone using a soluble rhenium compound.

11 Claims, No Drawings

DECOMPOSITION OF CUMENE HYDROPEROXIDE WITH A HOMOGENEOUS CATALYST

FIELD OF THE INVENTION

This invention relates to the catalytic cleavage of cumene hydroperoxide to equal molar portions of phenol and acetone.

DESCRIPTION OF THE PRIOR ART

Cumene can be readily oxidized with air to form cumene hydroperoxide and the hydroperoxide can then be decomposed to form equal molar amounts of phenol and acetone. In the commercial process for producing phenol by this general method, a small amount of a mineral acid, generally sulfuric acid, is used as the decomposition or cleavage catalyst. Since phenol and acetone are the products of the cleavage reaction, the reaction solvent can conveniently be a phenol-acetone solution. In this process the cumene hydroperoxide instantaneously decomposes to phenol and acetone as it is slowly added in solution with cumene to the mineral acid solution. The highly exothermic reaction is controlled by the rate of cumene hydroperoxide addition and by acetone reflux. Water is substantially excluded from the reaction medium to insure homogeneity. These processing details are essentially described in U.S. Pat. No. 2,663,735.

U.S. Pat. No. 3,351,635, relating to the epoxidation of olefins using hydroperoxide such as cumene hydroperoxide, discloses in Example 15 that rhenium heptoxide catalyzes the decomposition of hydroperoxide with 80 percent yield to decomposition products. This teaching that rhenium heptoxide is a hydroperoxide decomposition catalyst is covered in Japanese Application No. 51-80830, published July 15, 1976. In this published application rhenium heptoxide is specified as a catalyst for the decomposition of cumene hydroperoxide in an inert solvent. Phenol and phenol-acetone mixtures are excluded as a solvent component. The decomposition of cumene hydroperoxide is described by the Japanese application as taking 30 minutes to complete at about 100° C. in contrast to the substantially instantaneous decomposition of the acid-catalyzed commercial processes, but advantageously, this rhenium catalyzed process, as described, produces a phenol-acetone mixture with less undesirable impurities including less tar-like impurities than the acid-catalyzed processes.

SUMMARY OF THE INVENTION

Phenol is not an inert solvent for cumene hydroperoxide. Rather phenol, by virtue of its acid nature, has been found to be a catalyst for the decomposition of cumene hydroperoxide in a reaction which is significantly slower than the above-described mineral acid catalyzed reaction. Moreover, the selectivity of this phenol catalyzed decomposition of cumene hydroperoxide is very poor, being less than 80 percent selectivity to phenol as determined by our study of the reaction. It is readily apparent that the presence of solvent phenol in the mineral acid catalyzed reaction of the commercial processes is not noticeably detrimental because the great speed of the mineral acid catalyzed decomposition effectively eliminates the detrimental effect on selectivity of the relatively slow phenol catalyzed reaction. But a significant adverse affect on selectivity would be expected from solvent phenol in the relatively slow rhenium catalyzed reaction as suggested by the exclusion of phenol as a reaction solvent in the Japanese application.

Notwithstanding this detrimental effect of phenol on the decomposition of cumene hydroperoxide, we have surprisingly discovered in accordance with our invention that phenol, and more particularly a mixture of phenol and acetone, can be effectively used as a reaction medium for the catalytic cleavage of cumene hydroperoxide using a homogeneous rhenium catalyst such as rhenium heptoxide. In our process the decomposition reaction proceeds with very high selectivity to phenol and acetone, even substantially higher selectivity than resulting from mineral acid catalyzed decompositions. According to our discovery, we have found that the non-selective phenol catalyzed decomposition of cumene hydroperoxide can be minimized while retaining a substantial rate of the highly selective rhenium-catalyzed cleavage of the cumene hydroperoxide by careful control of the reaction conditions within critical limits. Furthermore, we have found that these reaction conditions are such that they advantageously permit the operation of this novel process in existing cumene-to-phenol commercial plants.

This invention is based in part on the discovery that the phenol catalyzed decomposition reaction is significantly more temperature dependent than the rhenium catalyzed decomposition reaction. That is, as the temperature is lowered, other conditions remaining the same, the rate of the phenol catalyzed decomposition drops much more rapidly than the rate of the rhenium catalyzed reaction permitting the cumene hydroperoxide to selectively decompose to phenol and acetone. We have also discovered that in the presence of very minute amounts of a soluble rhenium compound, the rate of the cleavage reaction is substantially affected by minor variations in the amount of the rhenium compound.

We have found, in particular, that we can successfully use phenol as a component of the reaction solvent by carefully correlating the temperature of the reaction mixture, the amount of the soluble rhenium compound in the cumene hydroperoxide-phenol-acetone solution and the time that the reaction mixture is heated, and that by this correlation a suitable rate of cleavage of the cumene hydroperoxide can be maintained using a minimum amount of the costly rhenium compound with minimum decomposition to undesired products.

This desired decomposition of the cumene hydroperoxide is a cleavage to equal mols of phenol and acetone, that is, about 62 weight percent phenol and 38 weight percent acetone. In using sulfuric acid as the decomposition catalyst, a selectivity to phenol of about 85 to 95 percent is generally obtained. The non-selective decomposition product particularly, as catalyzed by a strong mineral acid includes cumyl alcohol, acetophenone, methyl benzofuran, organic acids, cumyl phenols, alpha-methylstyrene and various oligomers of alpha-methylstyrene which are tar-like substances. Since few of these by-products of the non-selective reaction can be economically recovered, this non-selective reaction represents a significant economic loss.

A particular advantage in the use of the rhenium catalyst is that a selectivity greater than 90 percent, approaching 100 percent under optimum conditions, can be obtained. Another advantage of the rhenium catalyst in contrast with the strong mineral acid catalyst is that the rhenium catalyst is a non-acidic catalyst which does not promote the alkylation of phenol product to cumyl phenol nor the oligomerization of aromatic olefin to form tars. Furthermore, in the rhenium catalyzed reaction the major by-product, alpha-methylstyrene, is recovered and hydrogenated to cumene for recycle in the process. A further advantage in the use of the rhenium catalyst instead of the mineral acid is that the corrosion problems, neutralization procedures and the waste handling problems of the latter are substantially avoided. A particular advantage in the use of a phenol-acetone mixture as the reaction solvent is that final separation is simplified since phenol and acetone are also the product of the decomposition.

The preferred catalyst in our process is rhenium heptoxide, $Re_2O_7$. This compound is soluble in the phenol-acetone solvent forming a homogeneous catalyst system. Other soluble rhenium compounds can be used as a homogeneous catalyst such as rhenium carbonyl, $Re_2(CO)_{10}$, which it is believed oxidizes to the soluble rhenium oxide in the presence of the cumene hydroperoxide. We have found that the cleavage of cumene hydroperoxide can be effectively carried out using at least about 20 p.p.m. of rhenium heptoxide (parts per million parts of the total reaction mixture), more preferably at least about 25 p.p.m. rhenium heptoxide and most preferably about 30 p.p.m. rhenium heptoxide. The maximum amount of rhenium heptoxide that we use in our process is about 60 p.p.m., more preferably about 50 p.p.m. and most preferably a maximum of about 40 p.p.m. The rhenium compound can conveniently be dissolved in acetone or other inert solvent to aid in metering this small amount of catalyst into the reactor. Since rhenium is a very costly metal, it is desirable, in general, that a minimum amount, consistent with operating a practical process, be used to minimize the cost of rhenium losses and/or rhenium recovery procedures.

The solvent used in this process comprises phenol and acetone. Although the solvent can conveniently be the 1:1 phenol to acetone product of the cumene hydroperoxide cleavage reaction, variations in the relative proportions can be used. Thus, although there is no particular advantage to using an excess of phenol, an excess of acetone may be desirable particularly if the acetone is to be utilized for temperature maintenance through acetone boil-off or reflux. Therefore, the mol ratio of acetone to phenol in the reaction mixture may be as high as about 10:1 and preferably no higher than about 3:1.

We have found that the temperature of the decomposition reaction must be maintained within critical limits in order to obtain satisfactory cleavage of the cumene hydroperoxide with minimum undesirable by-products. If a temperature much in excess of 80° C. is utilized for the decomposition reaction, then the undesirable phenol catalyzed reaction tends to become excessive. Therefore, a maximum reaction temperature of about 80° C. is used, more preferably a maximum temperature of about 70° C. and most preferably a maximum temperature of about 65° C. A minimum temperature of at least about 40° C. has been found necessary to obtain a suitable rate of the desired cleavage reaction without using an excessive quantity of the costly rhenium catalyst, while a minimum temperature of at least about 50° C. is more preferred and a minimum temperature of at least about 55° C. is most preferred. The pressure within the reactor is not a critical factor during the decomposition reaction. Generally, the pressure will range from a pressure moderately below to moderately above atmospheric pressure.

We have also found it necessary that the reaction liquid be heated within a time constraint to obtain substantially complete conversion at high selectivity. Substantially complete conversion of the cumene hydroperoxide at high selectivity is obtained in our reaction by suitable correlation of the reaction parameters, as discussed, in which the reaction liquid is heated for a minimum of at least about one minute, more preferably at least about two minutes, and most preferably at least about five minutes and is heated for a maximum of about one hour, preferably a maximum of about 45 minutes and most preferably a maximum of about 30 minutes. This specified heating time refers to the time of heating the reaction liquid, whether in a batch reaction or in a semi-continuous or a continuous operation, to substantially complete decomposition of the cumene hydroperoxide. If there were any significant quantity of unreacted cumene hydroperoxide present in the final reaction product, it could undesirably interfere with the subsequent distillative separation.

The cumene hydroperoxide can desirably be prepared by oxidation of cumene with air in the conventional manner. In this process a solution of about 10 to 30 weight percent cumene hydroperoxide in cumene is produced. It is not particularly desirable to use this large amount of cumene in a continuous process as a reaction solvent due to subsequent handling and separation problems, therefore, the cumene hydroperoxide to be used in the decomposition reaction is preferably obtained by flashing off sufficient cumene to form a feed solution of between about 60 to about 90 percent, preferably about 65 to about 80 percent, cumene hydroperoxide. Although pure cumene hydroperoxide can be used, it is not desirable to obtain it in this final stage of purity for economic reasons and also for safety reasons since the presence of some cumene tends to stabilize the cumene hydroperoxide. The decomposition reaction can suitably be carried out with as little as about 0.1 weight percent cumene hydroperoxide in the reaction liquid, with at least about 0.5 percent being preferred and at least about 1.0 percent being most preferred. The maximum amount of cumene hydroperoxide in the cleavage reaction liquid will suitably be about 20 weight percent, preferably about 10 percent and most preferably about 5 percent.

As stated above, the various reaction conditions must be correlated in order to obtain satisfactory decomposition when phenol is used as a component of the reaction solvent. For example, at the minimum temperature the minimum amount of the catalyst cannot be used for an acceptable rate of decomposition, rather an amount of catalyst approaching the high end of the range will be required at the minimum temperature. If rapid reaction is desired, operation at minimum temperature or catalyst concentration is not feasible. The necessary correlation of processing details will become more apparent from the following specific examples which will serve as a guide for determining how to vary the reaction parameters for any desired result.

DESCRIPTION OF PREFERRED EMBODIMENTS

Example 1

The catalytic activity of sulfuric acid for the decomposition of cumene hydroperoxide was observed. A 57.3 percent solution of cumene hydroperoxide in cumene was added dropwise into 100 ml. of a two percent solution of sulfuric acid in acetone in a 300 ml. round bottom flask open to the atmosphere. Each drop instantly decomposed as it contacted the solution. Since no positive cooling of the reaction liquid was provided, the temperature of the solution rose from room temperature (about 25° C.) at the beginning of the addition to 44° C. upon the completion of the addition. A total of 35.2 g. of the cumene hydroperoxide was added over 60 minutes. Analysis of the product showed that 99.9 percent of the cumene hydroperoxide had reacted at a selectivity of 93 percent to phenol.

The reactions described in Examples 2 and 3 were carried out in a glass reactor equipped with a magnetic stirrer and operated at a pressure within the reactor slightly above atmospheric pressure. The reactor was cooled by a cold finger in the liquid. Small samples of the reaction liquid (about 1 ml.) were periodically withdrawn to monitor the reaction. The product was analyzed by titration for active oxygen, by gas chromatography and by high performance liquid chromatography.

Example 2

Phenol was tested as a decomposition catalyst for cumene hydroperoxide at several temperatures. About 20 g. of a solution consisting of 5 parts phenol, 3 parts acetone and 1 part cumene were placed in the reactor. About 2 ml. of a solution consisting of 55 percent cumene hydroperoxide in cumene were injected into the reactor in each experiment. Table I summarizes the results of these experiments.

TABLE I

| Temp. | Cumene Hydroperoxide Decomposed, % | | | |
|---|---|---|---|---|
| | Minutes | | | |
| | 10 | 20 | 50 | 100 |
| 40° C. | trace | trace | trace | trace |
| 60° C. | — | 8 | 19 | 39 |
| 80° C. | 18 | 34 | 60 | 85 |

The experiment at 80° C. was allowed to run for four and one-half hours at which time the cumene hydroperoxide was completely decomposed. Analysis of this product mixture disclosed that it contained 77 percent phenol, 8 percent alpha-methylstyrene, 4 percent acetophenone, 4 percent dimethylbenzyl alcohol, and 7 percent of a residuum consisting of aromatic carbonyls, aromatic alcohols, substituted phenols, substituted benzofurans and methylstyrene oligomers.

Example 3

A series of experiments was carried out at different temperatures, namely 40° C., 60° C., and 80° C., to determine the catalytic activity of rhenium heptoxide, $Re_2O_7$, as a decomposition catalyst for cumene hydroperoxide. As in the preceding example, a 20 g. solution consisting of 5 parts phenol, 3 parts acetone and 1 part cumene was placed in the reactor and 2 ml. of a 55 percent solution of cumene hydroperoxide in cumene were injected into the reactor. Immediately following this a 0.006 M solution of rhenium heptoxide in tetrahydrofuran was injected into the reactor. The results of these experiments are summarized in Tables II to IV:

TABLE II

| $Re_2O_7$, ppm. | Cumene Hydroperoxide Decomposed at 40° C., % | | | | |
|---|---|---|---|---|---|
| | Minutes | | | | |
| | 5 | 15 | 20 | 30 | 90 |
| 30 | 0 | <1 | <2 | 2 | 8 |
| 60 | 84 | 97 | 100 | — | — |

TABLE III

| $Re_2O_7$, ppm. | Cumene Hydroperoxide Decomposed at 60° C., % | | | | |
|---|---|---|---|---|---|
| | Minutes | | | | |
| | 5 | 10 | 15 | 60 | 90 |
| 20 | 6 | — | 13 | 29 | 38 |
| 30 | — | 100 | — | — | — |

TABLE IV

| $Re_2O_7$, ppm. | Cumene Hydroperoxide Decomposed at 80° C., % | | | | |
|---|---|---|---|---|---|
| | Minutes | | | | |
| | 10 | 20 | 35 | 50 | 70 | 105 |
| 10 | 28 | 39 | 56 | 70 | — | 96 |
| 20 | 75 | 84 | 91 | 96 | 100 | — |
| 30 | 100 | — | — | — | — | — |

Example 4

A larger scale decomposition reaction was carried out in a five gallon glass reactor equipped with a stirrer and cooling and heating coils. To this was charged 3,748 g. of phenol, 1,658 g. of acetone and 1,030 g. of cumene. The solution was heated to 60° C. and a solution of 210 mg. of rhenium heptoxide in 200 ml. of acetone was injected into the reactor. Immediately following the catalyst injection a solution of 362 g. of cumene hydroperoxide and 200 g. of cumene was injected into the reactor. There were 30 parts of the catalyst in the reactor per million parts of the total reaction solution. In five minutes the cumene hydroperoxide was completely decomposed. The temperature of the reaction liquid had risen to 65° C. during this reaction period. Analysis of the reaction product showed that the aromatic moiety of the cumene hydroperoxide had decomposed to 98 percent phenol, 1.8 percent alpha-methylstyrene and 0.2 percent acetophenone.

In a preferred procedure for decomposing cumene hydroperoxide by our method, the cumene hydroperoxide-cumene mixture and the solution of rhenium catalyst are continuously fed to the reactor which contains primarily phenol-acetone solvent and a minor amount of cumene. A product stream, in which the cumene hydroperoxide is substantially decomposed, is continuously removed from the reactor and separated by distillation into its various components. Part of the acetone is recycled as desired. The rhenium can be recovered from the distillation bottoms for reuse.

It is to be understood that the above disclosure is by way of specific example and that numerous modifications and variations are available to those of ordinary skill in the art without departing from the true spirit and scope of the invention.

We claim:

1. The method for cleaving cumene hydroperoxide at high selectivity approaching 100 percent to phenol and acetone using a homogeneous rhenium catalyst which comprises adding cumene hydroperoxide to a solution consisting essentially of phenol and acetone at a mol ratio of phenol to acetone of from about 1:1 to about 1:10 and up to about 15 weight percent cumene in an amount to form a reaction solution having between about 0.1 and about 20 weight percent cumene hydroperoxide, heating said reaction solution of cumene hydroperoxide, phenol and acetone in the presence of a rhenium catalyst consisting essentially of about 20 to about 60 parts of a soluble rhenium compound determined as rhenium heptoxide per million parts of the total reaction mixture for an average time of about one to about 60 minutes at a temperature between about 40° C. and about 80° C., and correlating the temperature, the concentration of rhenium compound and the average reaction time within said ranges whereby decomposition of the cumene hydroperoxide to phenol and acetone results with minimum decomposition to undesired products.

2. The method in accordance with claim 1 in which the said reaction solution is heated for an average of about five to about 30 minutes.

3. The method in accordance with claim 1 in which said reaction solution comprises from about 0.5 to about 10 weight percent cumene hydroperoxide.

4. The method in accordance with claim 1 in which said reaction solution comprises from about one to about five weight percent cumene hydroperoxide.

5. The method in accordance with claim 1 in which the ratio of phenol to acetone is between about 1:1 to about 1:3.

6. The method in accordance with claim 1 in which the ratio of phenol to acetone is about 1:1.

7. The method in accordance with claim 1 in which the said reaction solution is heated at a temperature between about 50° and 70° C.

8. The method in accordance with claim 1 in which the said reaction solution is heated at a temperature between about 55° and 65° C.

9. The method in accordance with claim 1 in which the said reaction solution comprises between about 25 and about 50 parts of rhenium determined as rhenium heptoxide per million parts of the total reaction solution.

10. The method in accordance with claim 1 in which the said reaction solution comprises between about 30 and about 40 parts of rhenium determined as rhenium heptoxide per million parts of the total reaction solution.

11. The method in accordance with claim 1 in which the said reaction solution is heated for an average of about two to about 45 minutes.

* * * * *